United States Patent
Liang et al.

(10) Patent No.: US 11,986,491 B2
(45) Date of Patent: *May 21, 2024

(54) PHARMACEUTICAL COMPOSITIONS COMPRISING IODINE AND STEROID AND USES THEREOF FOR SINUS DISEASES

(75) Inventors: Bo Liang, Plainsboro, NJ (US); Belachew Tessema, Famington, CT (US); Joseph A. Capriotti, Las Palmas (ES); Michael C. Samson, New York, NY (US); Wei Song, Jiangsu (CN)

(73) Assignee: IVIEW THERAPEUTICS, INC., Cranbury, NJ (US)

( * ) Notice: Subject to any disclaimer, the term of this patent is extended or adjusted under 35 U.S.C. 154(b) by 88 days.

This patent is subject to a terminal disclaimer.

(21) Appl. No.: 14/127,846

(22) PCT Filed: Jun. 22, 2011

(86) PCT No.: PCT/US2011/041470
§ 371 (c)(1),
(2), (4) Date: Mar. 14, 2014

(87) PCT Pub. No.: WO2012/177251
PCT Pub. Date: Dec. 27, 2012

(65) Prior Publication Data
US 2014/0219949 A1  Aug. 7, 2014

(51) Int. Cl.
| | | |
|---|---|---|
| A61K 31/79 | (2006.01) |
| A61K 9/00 | (2006.01) |
| A61K 31/38 | (2006.01) |
| A61K 31/56 | (2006.01) |
| A61K 31/573 | (2006.01) |
| A61K 31/58 | (2006.01) |
| A61P 11/00 | (2006.01) |

(52) U.S. Cl.
CPC ............ *A61K 31/79* (2013.01); *A61K 9/0043* (2013.01); *A61K 31/38* (2013.01); *A61K 31/56* (2013.01); *A61K 31/573* (2013.01); *A61K 31/58* (2013.01)

(58) Field of Classification Search
CPC ...... A61K 31/79; A61K 9/0043; A61K 31/56; A61K 31/573; A61K 31/58; A61P 11/00
See application file for complete search history.

(56) References Cited

U.S. PATENT DOCUMENTS

| | | | | |
|---|---|---|---|---|
| 5,492,937 A | * | 2/1996 | Bogentoft | A61K 8/731 |
| | | | | 424/426 |
| 6,241,969 B1 | * | 6/2001 | Saidi | A61K 31/58 |
| | | | | 424/45 |
| 6,565,832 B1 | * | 5/2003 | Haslwanter | A61K 9/0043 |
| | | | | 424/434 |
| 7,767,217 B2 | * | 8/2010 | Samson | A61P 27/02 |
| | | | | 424/405 |
| 8,163,723 B2 | * | 4/2012 | Lulla | A61K 31/55 |
| | | | | 514/171 |
| 8,562,963 B2 | * | 10/2013 | Samson | A61K 31/573 |
| | | | | 424/78.04 |
| 8,765,724 B2 | * | 7/2014 | Samson | A61K 33/18 |
| | | | | 424/405 |
| 9,387,223 B2 | * | 7/2016 | Samson | A61K 31/24 |
| 10,849,928 B2 | * | 12/2020 | Samson | A61K 31/24 |
| 2004/0204399 A1 | | 10/2004 | Osbakken et al. | |
| 2006/0280809 A1 | * | 12/2006 | Leshchiner | A61K 9/0043 |
| | | | | 424/672 |
| 2009/0186105 A1 | * | 7/2009 | Reiner | A61K 36/61 |
| | | | | 424/736 |
| 2009/0263345 A1 | | 10/2009 | Capriotti et al. | |
| 2010/0168074 A1 | | 7/2010 | Culligan et al. | |
| 2019/0269611 A1 | * | 9/2019 | Liang | A61K 47/10 |

FOREIGN PATENT DOCUMENTS

| | | | |
|---|---|---|---|
| CN | 102078325 | * | 6/2011 |
| CN | 102078325 A | * | 6/2011 |
| WO | WO200018404 A1 | * | 4/2000 |
| WO | WO 2008137658 | * | 11/2008 |

OTHER PUBLICATIONS

Cayman Chemicals, Product information; Desonide, (Year: 2022).*
IPR re PCT/US2011/041470, dated Dec. 23, 2013, 1 pg.
Search Report and Written Opinion re PCT/US2011/041470, mailed Apr. 6, 2012, 4 pgs.

* cited by examiner

*Primary Examiner* — Mina Haghighatian
(74) *Attorney, Agent, or Firm* — Weisun Rao; Jun Chen; Venture Partner, LLC

(57) ABSTRACT

The present invention provides pharmaceutical compositions comprising an iodine-containing compound and a steroid, useful for treating a clinical symptom in a patient's airway (e.g., nose, lung, and sinus), as well as methods for using the same.

7 Claims, No Drawings

PHARMACEUTICAL COMPOSITIONS COMPRISING IODINE AND STEROID AND USES THEREOF FOR SINUS DISEASES

CROSS-REFERENCE TO RELATED APPLICATION

This application is a national phase application and claims benefit, under 35 U.S.C. § 371, of PCT/US2011/041470, filed on Jun. 22, 2011, the contents of which are incorporated herein by reference in their entirety.

BACKGROUND OF THE INVENTION

Chronic rhinosinusitis (CRS) is a common clinical problem with significant morbidity and often-refractory symptoms that accounts for approximately 26.7 million office and emergency visits per year in the U.S. Originally part of the yogic and ayurvedic traditions, sinonasal irrigation is an adjunctive therapy for sinusitis and sinus symptoms that flushes the nasal cavity, facilitating a wash of the structures within. Several randomized controlled trials examining irrigation suggest that it is a safe, effective, and tolerable therapy for acute and chronic sinus symptoms. Previous studies have reported improvement of quality of life scores, symptom scores, and improvement of several other measures.

Current literature on chronic rhinosinusitis is centered around a multifactorial etiology, with the importance of fungus, bacteria, bacterial superantigens, allergic rhinitis, aspirin sensitivity, and organistic biofilms all being recognized. A common clinical sign of each of these is increased inflammation resulting in symptoms of postnasal drainage, congestion, pain, pressure, fatigue and thickened nasal discharge. These symptoms are especially heightened in those patients who remain symptomatic despite technically proficient endoscopic sinus surgery, in which pooling of mucin within open ethmoid and maxillary cavities often accompanies mucosal inflammation.

The most common agents implicated in acute viral rhinosinusitis include rhinovirus, influenza virus, and parainfluenza virus. Community-acquired acute bacterial rhinosinusitis is usually due to *Streptococcus pneumoniae* and *Haemophilus influenzae*. In chronic sinusitis, the infecting organisms vary, and a higher incidence of anaerobic organisms is seen including *Bacteroides, Peptostreptococcus*, and *Fusobacterium* species. In children, similar organisms are seen, with the addition of *Moraxella catarrhalis*. In older children and young adults, *Staphylococcus aureus* is also a causative agent. Nosocomial sinusitis presenting as fever of unknown origin can be seen in patients with prolonged intensive care unit stays or intubation. These patients are at risk of infection with gram-negative organisms including *Pseudomonas aeruginosa, Klebsiella pneumoniae, Enterobacter* species, *Proteus mirabilis*, and *Serratia marcescens*. Gram-positive cocci such as *Staph. aureus* can also be seen. Acute invasive fungal rhinosinusitis can be caused by *Candida, Aspergillus*, and *Phycomycetes* species. Risk factors include diabetes mellitus, cancer, hepatic disease, renal failure, burns, extreme malnutrition, and other immunosuppressive diseases. Diseases that compromise airway function, particularly cystic fibrosis, dramatically increase the risk and severity of sinusitis across all pathogen species with a greatly increased incidence of *Pseudomonas*.

Biofilms are commonly present in cases of chronic rhinosinusitis requiring surgery. Biofilm formation has been demonstrated by many bacterial species including *Pseudomonas aeruginosa, Staphylococcus aureus, Streptococcus pneumoniae, Haemophilus influenzae*, and *Moraxella catarrhalis*. Bacteria growing in biofilms are more resistant to antibiotics than their planktonic counterparts. Some of the mechanisms involved in biofilm resistance to antimicrobials may differ from the mechanisms responsible for antimicrobial resistance in planktonic bacteria, rendering traditional antibiotics less potent. The precise mechanism for biofilm antibiotic resistance is incompletely understood. Theories include a combination of restricted antibiotic penetration through the biofilm extracellular matrix, reduced metabolic activity, slower growth rate along different growth curves, and the up-regulation of efflux pumps.

Cystic fibrosis (CF) is a hereditary disease caused by a mutation in the gene for the protein cystic fibrosis transmembrane conductance regulator (CFTR). This gene codes for an ion channel that is required to regulate the components of sweat, digestive secretions and mucus. Mutations in the CFTR gene cause the production of abnormally functioning ion channels affecting certain glands in the mucus membranes, causing those glands to that produce thick, sticky mucus. It mainly affects organs such as the lungs, airways, sinuses, and digestive tract. This condition occurs in the sino-nasal cavity and promotes recurrent sinus infections and polyp formation when the gene responsible for manufacturing an ion channel becomes mutated, causing the gene to work abnormally. This ion channel is important for the healthy function of mucus, digestive juices and sweat. When this gene mutates it tells the body to produce thick, sticky mucus which promotes sinus conditions, upper airway disease and lower airway disease.

Chronic sinusitis in cystic fibrosis can cause multiple symptoms, including fever, runny nose, facial pain, headaches, nasal airway blockage and congestion due to the inflammatory changes of the sinonasal mucus membrane. One in every four patients who have cystic fibrosis develops nasal polyps. Chronic sinusitis with polyps is the most common clinical presentation of a patient with cystic fibrosis.

Since there is no cure for cystic fibrosis, an effort should be made to maintain the functionality of the upper airway and to minimize symptoms of reactive airway exacerbation due to recurrent infections. Recent studies have shown that the two main species that cause airway disease appear to be *pseudomonas* and *staphylococcus*. Furthermore, it is believed that these two organisms form biofilm and planktonic infections within the sinonasal cavity and airways. This bacterial and fungal biofilm and planktonic colonization can become a reservoir for sustained recurrent pulmonary infections.

Thus, the treatment of patients with cystic fibrosis should be aimed at eradicating the reservoir of microbial biofilm, reducing the inflammatory changes of the sinonasal cavity and recurrent sinus infection. There are two main ways this can be achieved successfully. Topical irrigation with anti-inflammatory and anti-microbial agents can also mechanically debride the thick mucin that obstructs the sinonasal drainage pathway. Moreover, for patient with advanced disease, functional endoscopic sinus surgery combined with topical therapy can achieve the same result. Furthermore, the use of biodegradable "sinus gel" that has dilute agents with antimicrobial and anti-inflammatory properties that can provide a protective layer can decrease the risk of postoperative biofilm colonization in patient with dysfunctional mucociliary clearance.

Earlier studies have shown a correlation between sinus disease quality of life and scores of forced expiratory volume in 1 second (FEV1) in children younger than 12 years. Adult patients with cystic fibrosis have been shown to have a statistically significant improvement in forced vital capacity (FVC) and FEV1 as well as fewer postsurgical hospitalization and hospital admission for pulmonary exacerbation following sinus surgery.

Iodine and steroid have both been used in treating nasal conditions or diseases. Most iodine preparations are toxic at useful concentrations, with the exception of iodophoric agents like povidone-iodine. It has been widely known that iodine or iodine-releasing agents (e.g., iodophor) are incompatible with most steroid preparations due to the high potential for chemical reactivity between molecular iodine and steroid moieties. As a result, these agents must be made from separate solutions, administered independently, requiring one or more preservatives typically used to stabilize preparations based on these two types of compounds. Commonly used preservatives include benzalkonium can cause bronchoconstriction, impairment of ciliary beat frequency and other unwanted effects in patients using preservative-containing steroids. However, studies have confirmed the possible harmful effects of conventional preservatives in solutions and suspensions. Additional in vitro studies have demonstrated that benzalkonium preservatives can damage the ciliary epithelium of the nose and sinuses.

These shortcomings demonstrate the need for better pharmaceutical preparations based on iodine and steroids that can be used for effective treatment of sinal conditions or diseases, including those discussed above.

SUMMARY OF THE INVENTION

In one aspect, this invention provides pharmaceutical compositions for treating a sinus symptom of a patient each including an iodine-containing compound and a steroid.

Though the reactivity of iodine with steroids is well known, the pharmaceutical compositions of this invention are surprising stable, as the steroids contained therein (e.g., mometasone, fluticasone, budesonide, or a salt or adduct thereof) have been able to resist iodination, iodine oxidation and iodine-catalyzed addition reactions whether in solution, suspension or in the dry-powder state. Example of the iodine compounds include iodophors (e.g., complexed with povidone, organic polymers, alcohols, polyols, surfactants, surface active anions and cations, detergents, or others known in the art). See, e.g., U.S. Pat. Nos. 2,706,701; 2,826,532; 3,039,916; 2,860,080; 2,840,510; and 2,759,869.

Such surprisingly stable pharmaceutical compositions containing highly toxic iodine and anti-inflammatory steroids are capable of synergistically treating sinus symptoms and inhibiting or even eliminating biofilms without casing toxic inflammatory reactions of the sino-nasal tissues. Additionally, these compositions are able to limit the inflammatory cascade and eliminate microbial, fungal, and viral activators of inflammation because of their ability to safely deliver antiseptic iodine and minimally absorbed sinonasal steroids.

In some embodiments, the iodine-containing compound comprises an iodophor which includes iodine complexed with a solubilizing agent. Examples of suitable solubilizing agents comprise organic polymers, alcohols, polyols, surfactants, surface active anions, cations, or detergents. One example of the iodine-containing compound is povidone-iodine complex (PVP-I). Examples of a suitable steroid comprise mometasone, fluticasone, budesonide, a salt thereof, an ester thereof, or any combination thereof. In some further embodiments, steroid is budesonide or a salt or ester thereof, and at least 91% of steroid remains in the pharmaceutical composition after the pharmaceutical composition is stored at a temperature in the range of 5-40° C. for a month.

In some embodiments, the concentration of the povidone-iodine complex (PVP-I) in a fully constituted aqueous solution (which is ready for the intended uses of this invention, e.g., by irrigating or spraying into a patient's nasal cavity) ranges from 0.01% to 10% by weight/weight or weight/volume percentage, from 0.1% to 2.5% by weight/weight or weight/volume percentage, from 0.15% to 1.5% by weight/weight or weight/volume percentage, from 0.2% to 1.0% by weight/weight or weight/volume percentage, or 0.2% by weight/weight or weight/volume percentage.

In an embodiment, the PVP-I concentration is measured on a weight/weight basis with respect to the overall solid weight of the packaged preparation. In another embodiment, the PVP-I concentration is measured on a weight/volume basis with respect to the overall preparation when combined with water sufficient to form 250 mL of irrigant. In an embodiment, a preparation comprises a steroid compound selected from the group consisting of budesonide, fluticasone, ciclesonide and mometasone, all salts thereof, and any combination thereof.

In some embodiments, these pharmaceutical compositions may further include a tonicity agent (e.g., HCl, NaCl, $NaHCO_3$, or similar salts).

In some other embodiments, the pharmaceutical composition may further include a surfactant, a viscosity increasing agent, a bioadhesive agent, or a cooling agent. Examples of a suitable surfactant comprise polysorbate-20, polysorbate-60, polysorbate-80, polyoxyethylene surfactant, polyoxypropylene surfactant, cyclodextrin, tyloxapol, PEG 35 Caster oil, polyoxyl 40 Strerate, or any combination thereof. The surfactant in the pharmaceutical compositions can have a concentration ranging from 0.01% to 2% by weight. Examples of a suitable viscosity increasing agent include polyvinyl alcohol, polyvinylpyrrolidone, methyl cellulose, hydroxypropylmethylcellulose, hydroxyethylcellulose, carboxymethylcellulose, hydroxypropylcellulose, microcrystalline cellulose, carboxymethyl cellulose sodium, dextrose anhydrous, or any of their combinations. The concentration of the viscosity agent can range from 0.01% to 2% by weight. Examples of a suitable bioadhesive agent include polyvinylpyrrolidone, xanthan gum, locust bean gum, acacia gum, hydroxypropyl methylcellulose, sodium alginate, pectin, gelatin, carbomer, polyvinylalcohol, gellan gum, tragacanth, acacia, sodium carboxymethyl cellulose, or any of their combinations. Examples of a suitable cooling agent include menthol, methane glycerin acetyl, menthyl ester, carboxamide, menthane glycerol ketal, alkyl substituted urea, sulfonamide, terpene analogs franone, phosphine oxide, derivative thereof, camphor, bonel, or any of their combination.

In some other embodiments, the pharmaceutical compositions can be in the form of a solution (e.g., an aqueous solution), a suspension, an emulsion, a dry sterile powder, a controlled-release vehicle, or a sustained-release vehicle. They can be diluted or constituted with purified water or an aqueous saline, when needed and in situ, to give a low iodine concentration and subsequently administered to a patient in need thereof, e.g., by washing or irrigation of the patient's sinal cavity or by spraying into it. Examples of suitable devices for the dilution or constitution include those described in WO 2009/097123 A1.

Examples of the pharmaceutical compositions of this invention include: an aqueous solution containing about 10% (w/w) povidone-iodine, about 0.015% (w/w) micronized budesonide, micronized fluticasone proprionate, or micronized mometasone; an aqueous solution containing about 15% (w/w) povidone-iodine and about 0.025% (w/w) micronized budesonide, microcrystalline cellulose and carboxymethyl cellulose sodium; sodium chloride; polysorbate 80; disodium edetate; and hydrochloric acid, or sodium hydroxide; an aqueous solution containing about 15% (w/w) povidone-iodine, about 0.025% (w/w) micronized fluticasone proprionate aqueous suspension, microcrystalline cellulose and carboxymethyl cellulose sodium, sodium chloride, polysorbate 80, disodium edetate, hydrochloric acid, or sodium hydroxide; an aqueous solution containing about 15% (w/w) povidone-iodine, about 0.025% (w/w) micronized mometasone aqueous suspension, microcrystalline cellulose and carboxymethyl cellulose sodium, sodium chloride, polysorbate 80, disodium edetate, hydrochloric acid, or sodium hydroxide; an aqueous solution and comprises about 50% (w/w) povidone-iodine, about 7.5% (w/w) budesonide aqueous suspension, 8% (w/w) polysorbate 80; and 18 g NaCl. All of these can be readily diluted to form a solution for irrigating or spraying into the sinus cavity of a patient, e.g., at a total daily dose of about 1.0 mg budesoinde, about 1.0 mg fluticasone proprionate, or about 0.1 mg mometasone.

The compositions of this invention can be administered by employing an apparatus which includes a flexible bottle with an opening and conduit tube (such as that available commercially from NeilMed, Santa Rosa, CA). They are capable of providing iodophor in sufficient concentration to deliver molecular iodine at a low but sufficient level to adequately preserve the compositions or to adequately eliminate infectious organisms or to eliminate biofilms.

In another aspect, the invention provides a method for treating a clinical symptom of the airway of a patient, which includes administering to the patient's sinal cavity a pharmaceutical composition comprising an iodine-containing compound and a steroid.

In some embodiments, the clinical symptom of the airway is inflammation, infection, formation of biofilm, rhinosinusitis, congestion, pain, pressure, fatigue, or thickened nasal discharge in the sinus; or discomfort in the lung.

In some embodiments, the airway is sinus, nose, or lung.

In some other embodiments, the pharmaceutical compositions can each be formulated as an aqueous solution or a suspension. In some other embodiments, the pharmaceutical compositions can each have a pH value of from about 2.0 to about 7.5, from about 2.0 to about 7.0, from about 3.0 to about 6.0, or from about 4.0 to about 5.0.

In yet still some other embodiments, the pharmaceutical compositions can be administered by irrigating or spraying into the patient's sinus cavity. Such administration can be performed, e.g., through a rinsing bottle, metered-dose, manual-pump spray, a metering, or an atomizing spray pump.

In still some other embodiments, the iodine-containing compound comprises povidone-iodine, and the steroid comprises budesonide, micronized fluticasone proprionate, or micronized mometasone.

In some embodiments, the dose volume of the iodine-containing compound (e.g., PVP-I) administered to the patient can range from about 10 mcg to about 300 mcg per day, about 20 mcg to about 200 mcg per day, about 30 mcg to about 100 mcg per day, or about 50 mcg per spray with two spray per nostril per day.

In still another aspect, the invention provides a method for improving the lung condition of a cystic fibrosis patient, comprising washing the patient's sino-nasal cavity (i.e., through the nostril and up in to the sinus) with a pharmaceutical composition comprising an iodine-containing compound and a steroid.

In some embodiments, the iodine-containing compound comprises povidone-iodine.

In some other embodiments, the steroid comprises budesonide, micronized fluticasone proprionate, or micronized mometasone.

In yet still another aspect, the invention provides a method for stabilizing an iodine-containing compound at a low concentration, which includes mixing the iodine-containing compound with a steroid. The stability can be determined by the "Preservative Effectiveness Test" protocol as described in the United States Pharmacopeia.

Examples of the steroid include budesonide, micronized fluticasone proprionate, and micronized mometasone; whereas an example of the iodine-containing compound comprises povidone-iodine.

This method would provide a free iodine or providone-iodine concentration as low as in the range of from about 0.01% to about 10%, from about 0.1% to about 2.5%, from about 0.15% to about 1.5%, from about 0.2% to about 1.0%, or about 0.2% by weight/weight percentage or weight/volume percentage.

In addition to the clinical benefit derived from the use of non-toxic preservatives, the pharmaceutical compositions of this invention (with or without addition of a tonicity agent) are efficacious against a variety of bacteria, viruses and fungi that routinely contaminate non-sterile products and that are also frequent causes of infections. They are able to eliminate infection-causing organisms and simultaneously treat inflammation that is caused by said organisms. One class of organisms that can be eliminated with the formulations described are bacterial organisms. Others include viral organisms, fungal organisms, and protozoal organism. Particular bacterial organisms that can be eliminated by the described formulations include common *staphylococcus* species, resistant *staphylococcus* species, gram-negative bacteria, gram-positive bacteria, atypical bacteria and others.

The pharmaceutical composition of this invention have great utility in the treatment of nasal and sinus inflammation where infection may also be present, in the treatment of non-infectious inflammation where there is a potential to form biofilms, in the treatment of inflammation where there are existing biofilms that may be destroyed by the iodine component, in the treatment of mixed infection and inflammation where irrigation with a mixed steroid-iodine containing solution could treat both infectious and inflammatory components, allergic inflammation of the sinuses and nasal passages and other cases of and inflammation such as that which occurs after surgery. Further, they are self-preserved and require no additional agents for prolonged sterile storage, thus eliminating the need of using benzalkonium, imidurea, and other toxic preservatives.

Surprisingly, irrigating the sinuses with a pharmaceutical composition of this invention (e.g., povidone-iodine/budesonide) improves the clinical symptoms in all parts of the airway (sinus, nose and lungs). The data from using PVP/I budesonide in patient with cystic fibrosis has shown clinically and statistically significant improved patient outcome scores (SNOT 22) and reduction in bacterial load.

Another aspect of the invention includes methods for treating chronic rhinosinusitis or acute rhinosinusitis with the pharmaceutical compositions of this invention (e.g., iodophor-steroid combinations). A further aspect of the invention includes methods for treating sinonasal inflammation while inhibiting biofilm formation in patients with acute rhinosinusitis, chronic rhinosinusitis or recovering from sinus surgery with the same pharmaceutical compositions of this invention. Additionally the invention includes the methods for treating existing bacterial or fungal biofilms in patients with acute rhinosinusitis, chronic rhinosinusitis or recovering from sinus surgery with the same pharmaceutical compositions.

DETAILED DESCRIPTION OF THE INVENTION

In one aspect, the invention provides surprisingly stable pharmaceutical compositions for treating a sinal symptom which comprises an iodine-containing compound (e.g., povidone-iodine) and a steroid (budesonide, micronized fluticasone proprionate, or micronized mometasone).

In an embodiment, the invention provides a preserved steroid composition comprising a povidone-iodine composition. In an embodiment, the concentration of povidone-iodine as a preservative in steroid compositions can range from 0.01-10% (weight/weight or weight/volume), and all concentrations in between. In an embodiment, the povidone-iodine concentration is between 0.1% and 2.5%, in another embodiment, between 0.15 and 1.5%, and in yet another embodiment, between 0.2% and 1.0%. In an embodiment, the povidone-iodine concentration is about 0.2%.

These pharmaceutical compositions (e.g., containing povidone iodine and a steroid) possess antimicrobial property. Thus, in another aspect, an iodine-containing compound (e.g., povidone iodine) provides a steroid preparation with one or more non-antimicrobial preservative properties (e.g., antioxidant). In an embodiment, the invention also provides povidone-iodine compositions comprising one or more components in addition to the povidone-iodine component, as set forth herein. In an aspect, the invention provides a broad spectrum of povidone-iodine steroid compositions. In an embodiment, a preparation comprises an anti-inflammatory compound selected from the group consisting of budesonide, fluticasone, mometasone, all salts thereof, all esters thereof, and any combination thereof.

It is well known to those skilled in the art that more dilute solutions of PVP-I are more effective anti-microbial agents. It is useful to supply these PVP-I solutions to areas of infection and/or inflammation in the concentration range around 0.01% PVP-I (w/w) and about 1% PVP-I. However, the aqueous stability of PVP-I in dilute concentrations below 0.40% limits their long term storage. The iodine component of these dilute PVP-I preparations can often decay when the starting PVP-I concentration is much less than 0.4% (see, e.g., U.S. Pat. Nos. 4,976,969 and 4,996,048). We have developed a stable, chemically distinct suspension of PVP-I and steroid in small aqueous volumes for dilution into irrigating solutions to be employed in sinonasal irrigation. In this way we have developed stable solutions of PVP-I/steroids that can be used to deliver therapeutic steroid concentrations along with low-concentration PVP-I for therapeutic treatment of acute and chronic sinus infections. The compositions do not suffer from the long term instability of PVP-I low concentration preparations and yet still deliver an effective lower concentration of PVP-I to the intended area.

One example of the pharmaceutical compositions described above includes 400 mg PVP-I USP grade dry powder dissolved in 4 cc sterile water into which is suspended 0.6 mg of budesonide. This is supplied as a stable 4 cc vial for patients to keep in their homes. Prior to irrigation into the sinuses, approximately 200 cc of water is added to an 8 oz sinus irrigation bottle to make an irrigating solution of approximately 0.2% PVP-I aqueous concentration and still contains 0.6 mg suspended budesonide. In other examples, the steroid can be mometasone, fluticasone or other nasal steroids and the PVP-I can vary between 0.005 g and 1 g dissolved in 1 cc, 2 cc, 3 cc, 4 cc or any other small volume of suspendant suitable to suspend the steroid.

Additionally, non-limiting examples of suitable excipients for the pharmaceutical compositions of this invention include co-solvents, surfactants, viscosity agents, or bioadhesive agents. Furthermore, the compositions can be combined with an effective amount of a chemical agent to provide a cooling sensation to relieve mild irritation, enhance comfort, provide a refreshing effect, and improved sensation, when the povidone-iodine solution is applied. Such an agent encompasses various chemicals and chemical classes, including, but not limited to, cooling agents such as menthol, menthol derivatives including methone glycerin acetyl and menthyl esters, carboxamides, menthane glycerol ketals, alkyl substituted ureas, sulfonamides, terpene analogs, furanones, and phosphine oxides; or camphor, and borneol.

In an aspect, the compositions of the invention may optionally comprise a co-solvent. In an embodiment, the solubility of the components of the compositions may be enhanced by a surfactant or other appropriate co-solvent in the composition. Such co-solvents/surfactants include, but are not limited to, polysorbate-20, -60, and -80, polyoxyethylene/polyoxypropylene surfactants (e.g. Pluronic F-68, F-84 and P-103), cyclodextrin, tyloxapol, PEG 35 Caster oil (Cremophor EL), polyoxyl 40 Stearate (Myrj 52), as well as other agents known to those skilled in the art, or any combination thereof. Typically, such co-solvents are employed at a level of from about 0.01% to about 2% by weight.

In another aspect, the compositions of the invention may optionally comprise an optional viscosity-increasing agent. Viscosity increased above that of simple aqueous solutions may be desirable to increase absorption of the active compound, to decrease variability in dispensing the formulation, to decrease physical separation of components of a suspension or emulsion of the formulation and/or to otherwise improve the irrigating steroid formulation. Such viscosity-enhancing agents include, but are not limited to, polyvinyl alcohol, polyvinylpyrrolidone, methyl cellulose, hydroxypropylmethylcellulose, hydroxyethylcellulose, carboxymethylcellulose, hydroxypropylcellulose, microcrystalline cellulose, carboxymethyl cellulose sodium, dextrose anhydrous, other agents known to those skilled in the art, and/or any combination thereof. Such agents are typically employed at a level of from 0.01% to 2% by weight.

In another aspect, bioadhesive agents may comprise the compositions, in order to increase the retention time of the drug gradient over a biological substrate. The bioadhesive agents include, but are not limited to: polyvinylpyrrolidone (PVP), xanthan gum, locust bean gum, acacia gum, hydroxypropyl methylcellulose (HPMC), sodium alginate, pectin, gelatin, carbomer, polyvinylalcohol, gellan gum, tragacanth, acacia, and sodium carboxymethyl cellulose, as well as other agents known to those skilled in the art, or any combination thereof.

The povidone-iodine-comprising steroid composition may be in the form of a solution, a suspension, an emulsion, a dry sterile powder, or a controlled-release/sustain-release vehicle. It may be applied to a subject through metered-dose, manual-pump spray, or a metering, atomizing spray pump, or any inhalation device.

In any of the compositions of this disclosure for sinonasal inhalation administration, the mixtures are preferably formulated as aqueous solutions or suspensions at a pH in the range of 2.0 to 7.0. It will be understood that a range listed herein is intended to encompass the upper and lower bounds of the range, inclusively. In an embodiment, the pH is in the range of 4 to 5. This pH range may be achieved by the addition of acids/bases to the solution. In another embodiment, the pH is in the range of 3 to 6. In another embodiment, the pH is in the range of 3-6 and can be maintained at selected pH ranges of 1-2 pH unit from 2.0 to 7.5 through the use of appropriate buffers.

The invention also provides methods of using the pharmaceutical compositions described herein for treating a clinical symptom of the airway of a patient, e.g., by administering the compositions in the patient's sinal cavity. In an embodiment, the dose volume administered to the patient may range from about 10 mcg to about 300 mcg per day, from about 20 mcg to about 200 mcg per day, from about 30 mcg to about 100 mcg per day, or about 50 mcg per spray, two sprays per nostril once daily.

As used herein, the term "or" is meant to include both "or" and "and."

As used herein, the term "pharmaceutical compositions" is interchangeable with pharmaceutical preparation.

As used herein, the term "a patient" refers to a mammal, including animal or human being.

As used herein, the term "iodine-containing compound" is meant to include free iodine, complex or adduct containing iodine and capable of releasing iodine under certain conditions.

As used herein, the term "steroid" refers to anti-inflammatory steroids including corticosteroids. Specific examples include hydrocortisone, hydrocortisone acetate, cortisone acetate, tixocortol pivalate, prednisolone, methylprednisolone, and prednisone; triamcinolone acetonide, triamcinolone alcohol, mometasone, amcinonide, budesonide, desonide, fluocinonide, fluocinolone acetonide, and halcinonide; betamethasone, betamethasone sodium phosphate, dexamethasone, dexamethasone sodium phosphate, and fluocortolone; hydrocortisone-17-butyrate, hydrocortisone-17-valerate, aclometasone dipropionate, betamethasone valerate, betamethasone dipropionate, prednicarbate, clobetasone-17-butyrate, clobetasol-17-propionate, fluocortolone caproate, fluocortolone pivalate, and fluprednidene acetate; flunisolide; fluticasone propionate; triamcinolone acetonide; beclomethasone dipropionate, and budesonide.

As used herein, the term "tonicity agent" refers to an agent used to adjust the composition of the formulation to the desired isotonic range. Examples of tonicity agents include glycerin, mannitol, sorbitol, sodium chloride, and other electrolytes. See, e.g., U.S. Pat. No. 6,933,289.

As used herein, the term "surfactant" refers to a compound that lowers the surface tension of a liquid, the interfacial tension between two liquids, or that between a liquid and a solid. Some commonly encountered surfactants include: alkyl sulfates (e.g., ammonium lauryl sulfate, sodium lauryl sulfate); alkyl ether sulfates (e.g., sodium laureth sulfate, also known as sodium lauryl ether sulfate (SLES), sodium myreth sulfate); sulfonates (e.g., dioctyl sodium sulfosuccinate); sulfonate fluorosurfactants (e.g., perfluorooctanesulfonate, perfluorobutanesulfonate); alkyl benzene sulfonates; alkyl aryl ether phosphate; alkyl ether phosphate; alkyl carboxylates (e.g., fatty acid salts (soaps): sodium stearate); sodium lauroyl sarcosinate; carboxylate fluorosurfactants (e.g., perfluorononanoate, perfluorooctanoate); octenidine dihydrochloride; alkyltrimethylammonium salts (e.g., cetyl trimethylammonium bromide, cetyl trimethylammonium chloride); cetylpyridinium chloride; polyethoxylated tallow amine; benzalkonium chloride; benzethonium chloride; 5-bromo-5-nitro-1,3-dioxane; dimethyldioctadecylammonium chloride; dioctadecyldimethylammonium bromide; (3-[(3-Cholamidopropyl)dimethylammonio]-1-propanesulfonate); sultaines (e.g., cocamidopropyl hydroxysultaine); amino acids; imino acids; betaines (e.g., cocamidopropyl betaine); fatty alcohols (e.g., cetyl alcohol, stearyl alcohol, cetostearyl alcohol; oleyl alcohol); polyoxyethylene glycol alkyl ethers; octaethylene glycol monododecyl ether, pentaethylene glycol monododecyl ether; polyoxypropylene glycol alkyl ethers; glucoside alkyl ethers; decyl glucoside, lauryl glucoside, octyl glucoside; polyoxyethylene glycol octylphenol ethers; Triton X-100; polyoxyethylene glycol alkylphenol ethers; nonoxynol-9; glycerol alkyl esters; sorbitan alkyl esters; cocamide MEA, cocamide DEA; dodecyldimethylamine oxide; block copolymers of polyethylene glycol and polypropylene glycol.

As used herein, the term "treating" refers to reducing, either partially or completely, the severity of a symptom shown by a patient.

All references cited are incorporated herein by reference in their entireties.

The invention is now described with reference to the following Examples. These Examples are provided for the purpose of illustration only and the invention should in no way be construed as being limited to these Examples, but rather should be construed to encompass any and all variations which become evident as a result of the teaching provided herein.

Example 1

Preparation of PVP-I (0.2%), Budesonide (0.6 mg) Nasal Irrigation 400 mg PVP-I USP grade dry powder was dissolved in 4 g sterile water into which is suspended 0.6 mg of budesonide suspension, which may have or have not contained other excipients such as co-solvents/surfactants, bioadhesives, and tonicity agents. Prior to irrigation into the sinuses, approximately 200 mL of water was added to an 8 oz sinus irrigation bottle to QS 240 mL and made an irrigating solution of 0.2% PVP-I aqueous concentration and still contained 0.6 mg suspended budesonide.

Example 2

Preparation of PVP-1, Budesonide Suspension, 1.0 Mg

Budesonide suspension with PVP-I concentration ranging from about 0.25% by weight was prepared as set forth herein. By way of a non-limiting example, a composition was prepared using approximately 0.6 g PVP-I product, and combining with micronized budesonide 1.0 mg, microcrystalline cellulose and carboxymethyl cellulose sodium, polysorbate 80, disodium edetate, sodium chloride, and purified water; hydrochloric acid and/or sodium hydroxide was added to adjust the pH to a target of 4-6. To the above mixture was added water QS 240 mL. The resulting mixture was a 0.25% PVP-I, isotonic irrigating mixture that delivers a total daily dose of 1.0 mg budesoinde via sinonasal irrigation when completely administered in one day. The preparation was suitable for sinonasal irrigation or topical administration.

Example 3

Preparation of PVP-I, Fluticasone Proprionate Suspension, 1.0 Mg

Budesonide suspensions with PVP-I concentration ranging from about 0.25% by weight were prepared as set forth herein. By way of a non-limiting example, a composition was prepared using approximately 0.6 g PVP-I product, and combining with micronized fluticasone proprionate 1.0 mg, microcrystalline cellulose and carboxymethyl cellulose sodium, polysorbate 80, disodium edetate, sodium chloride, and purified water; hydrochloric acid and/or sodium hydroxide is added to adjust the pH to a target of 4-6. To the above mixture was added water QS 240 mL. The resulting mixture was a 0.25% PVP-I, isotonic irrigating mixture that delivered a total daily dose of 1.0 mg fluticasone proprionate via sinonasal irrigation when completely administered in one day. The preparation was suitable for sinonasal irrigation or topical administration.

Example 4

Preparation of PVP-I, Mometasone Suspension, 1.0 Mg

Budesonide suspension with PVP-I concentration ranging from about 0.25% by weight is prepared as set forth herein. By way of a non-limiting example, a composition is prepared using approximately 0.6 g PVP-I product, and combining with micronized mometasone 1.0 mg, microcrystalline cellulose and carboxymethyl cellulose sodium, polysorbate 80, disodium edetate, sodium chloride, and purified water; hydrochloric acid and/or sodium hydroxide is added to adjust the pH to a target of 4-6. To the above mixture is added water QS 240 mL. The resulting mixture is a 0.25% PVP-I, isotonic irrigating mixture that delivers a total daily dose of 1.0 mg mometasone via sinonasal irrigation when completely administered in one day. The preparation is suitable for sinonasal irrigation or topical administration.

Example 5

Antimicrobial Activity of PVP-I Preserved Steroid Solutions

By way of a non-limiting example, PVP-I Preserved Steroid Solutions were prepared according to methods described in Examples 1-4. These solutions were then tested for in-vitro microbiological activity. Microbiological activity can be tested for antimicrobial activity against, for example, bacteria found in the mouth (*P. gingivalis*), or against other bacteria. In another example, killing time tests were conducted with a series of log phase cultures of gram negative and gram positive organisms including Gentamicin resistant *Pseudomonas aerouginosa*, methicilin-resistant *staph aureus, E. coli*, chlamydia trachoma and selected viruses including adenoviruses and rhinoviruses. Controls used may include steroid preparations of commercially available antimicrobial products. Bacterial samples were taken at 30 seconds, 1, 2, 5, 10 and 15 minutes and transferred into culture media containing inactivators for iodine. Similarly, virus killing time tests were sampled at one minute and transferred into inactivating media. The results obtained with the experimental samples were compared with the control samples to assess the level of antimicrobial activity of a composition of the invention.

Example 6

Antimicrobial Preservative Effectiveness Test of PVP-I In Nasal Steroid Preparations By way of a non-limiting example, PVP-I Preserved Steroid Solutions were prepared according to methods described in Examples 1-4. These solutions were then tested for preservative effectiveness according to standard procedures described in the United States Pharmacopeia, General Chapter 51. The iodophor preservatives as prepared in Examples 1-4 were employed in such a way as to satisfy all requirements for preservative effectiveness as described by USP <51>.

Example 7

Preparation of PVP-I (10%), Budesonide (0.3 g) Nasal Irrigation 200 g PVP-I USP grade dry powder was dissolved in 4 g sterile water into which was suspended 0.3 g of budesonide suspension, then added 0.32 g polysorbate 80, 18 g NaCl, respectively. Water was added to the above mixture to 2000 g to give rise to an irrigating solution of 10% PVP-I aqueous concentration, with 0.3 g suspended budesonide.

Stability of the Solutions:

The amount of titratable iodine in the solutions was determined by titration method after 6 months of sample storage at different temperatures.

Titration Method:

5 mL of each sample was transferred into a 125 mL beaker by pipette, and 1 mL of 1% (w/v) starch indicator solution was added. The solution was titrated with 0.02 N sodium thiosulfate solution until the blue color disappeared completely. The volume of sodium thiosulfate solution used was determined.

$$\text{Titration Iodine (mg)} = 0.02 N * V(\text{mL, volume used for titration}) * 12.69 (\text{mg/mL})/2$$

TABLE 1

Stability Data Summary (Available Iodine at 5° C.)

| Day | Glass vial with spray pump cap Vertical Storage average % w/w iodine | Available iodine (%) | Glass vial with spray pump cap Horizontal Storage average % w/w iodine | Available iodine (%) | Glass vial with cap average % w/w iodine | Available iodine (%) |
|---|---|---|---|---|---|---|
| 0 day | 0.9719 | 100.0 | 0.9719 | 100.0 | 0.9719 | 100.0 |
| 15th day | 0.9687 | 99.67 | 0.9686 | 99.66 | 0.9639 | 99.17 |
| 1 month | 0.9740 | 100.22 | 0.9670 | 99.50 | 0.9635 | 99.14 |
| 3 months | — | — | — | — | 0.9541 | 98.17 |
| 6 months | | | | | 0.9546 | 98.22 |

TABLE 2

Stability Data Summary (Available Iodine at 25° C.)

| Day | Glass Vial with Spray pump cap Vertical Storage average % w/w iodine | Available iodine (%) | Glass Vial with Spray pump cap Horizontal Storage average % w/w iodine | Available iodine (%) | Glass Vial with Cap average % w/w iodine | Available iodine (%) |
|---|---|---|---|---|---|---|
| 0 day | 0.9719 | 100.0 | 0.9719 | 100.0 | 0.9719 | 100.0 |
| 15th day | 0.9561 | 98.37 | 0.9560 | 98.36 | 0.9581 | 98.58 |
| 1 month | 0.9782 | 100.60 | 0.9751 | 100.33 | 0.9768 | 100.50 |
| 2 months | — | — | — | — | 0.9523 | 97.98 |
| 3 months | — | — | — | — | 0.9515 | 97.90 |
| 6 months | | | | | 0.9524 | 98.01 |

TABLE 3

Stability Data Summary (Available Iodine at 30° C.)

| Day | Glass Vial with Spray pump cap Vertical Storage average % w/w iodine | Available iodine (%) | Glass Vial with Spray pump cap Horizontal Storage average % w/w iodine | Available iodine (%) | Glass Vial with Cap average % w/w iodine | Available iodine (%) |
|---|---|---|---|---|---|---|
| 0 day | 0.9719 | 100.0 | 0.9719 | 100.0 | 0.9719 | 100.0 |
| 15th day | 0.9553 | 98.29 | 0.9565 | 98.42 | 0.9513 | 97.88 |
| 1 month | 0.9592 | 98.69 | 0.9600 | 98.78 | 0.9577 | 98.54 |
| 3 months | — | — | — | — | 0.9452 | 97.05 |
| 6 months | | | | | — | — |

TABLE 4

Stability Data Summary (Available Iodine at 40° C.)

| Day | Glass Vial with Spray pump cap Vertical Storage average % w/w iodine | Available iodine (%) | Glass Vial with Spray pump cap Horizontal Storage average % w/w iodine | Available iodine (%) | Glass Vial with Cap average % w/w iodine | Available iodine (%) |
|---|---|---|---|---|---|---|
| 0 day | 0.9719 | 100.0 | 0.9719 | 100.0 | 0.9719 | 100.0 |
| 15th day | 0.9449 | 97.22 | 0.9442 | 97.15 | 0.9435 | 97.06 |
| 1 month | 0.9544 | 98.02 | 0.9567 | 98.44 | 0.9531 | 98.07 |
| 2 months | — | — | — | — | 0.9231 | 94.98 |
| 3 months | — | — | — | — | 0.9170 | 94.35 |

The data of available iodine content of the formulations after months of storage at different temperatures (5° C., 25° C., 30° C., 40° C.), have suggested that stable combination formulations have been achieved for PVP-Iodine combinations with budesonide. The available iodine content of the formulations at different temperatures showed no significant degradation after 6 months. The data showed excellent stability of the PVP-Iodine.

Stability Data of Budesonide Content in the Sample Using HPLC

The USP method was performed. The concentration of budesonide data is tabulated as follows.

TABLE 5

The stability of budesonide at 5° C. (content unit µg/mL):

| Day | Glass Vial with Spray pump cap Vertical Storage | Budesonide content (%) | Glass Vial with Spray pump cap Horizontal Storage | Budesonide content (%) | Glass Vial with Cap | Budesonide content (%) |
|---|---|---|---|---|---|---|
| 0 day | 150.0 | 100 | 150.0 | 100 | 144.0 | 100 |
| 15th day | 146.4 | 97.6 | 150.7 | 100.5 | 146.6 | 101.8 |
| 1 month | 146.5 | 97.7 | 152.3 | 101.5 | 144.8 | 100.6 |
| 3 months | — | — | — | — | 146.4 | 101.7 |
| 6 months | | | | | 146.0 | 101.5 |

TABLE 6

The stability of budesonide at 25° C. (content unit µg/mL):

| Day | Glass Vial with Spray pump cap Vertical Storage | Budesonide content (%) | Glass Vial with Spray pump cap Horizontal Storage | Budesonide content (%) | Glass Vial with Cap | Budesonide content (%) |
|---|---|---|---|---|---|---|
| 0 day | 150.0 | 100 | 150.0 | 100 | 144.0 | 100 |
| 15th day | 149.1 | 99.4 | 148.4 | 98.9 | 143.5 | 99.7 |
| 1 month | 149.3 | 99.5 | 145.7 | 97.1 | 145.7 | 101.2 |
| 2 months | — | — | — | — | 139.0 | 96.5 |
| 3 months | — | — | — | — | 139.6 | 97.0 |
| 6 months | | | | | 135.3 | 94.0 |

TABLE 7

The stability of budesonide at 30° C. (content unit µg/mL):

| Day | Glass Vial with Spray pump cap Vertical Storage | Budesonide content (%) | Glass Vial with Spray pump cap Horizontal Storage | Budesonide content (%) | Glass Vial with Cap | Budesonide content (%) |
|---|---|---|---|---|---|---|
| 0 day | 150.0 | 100 | 150.0 | 100 | 144.0 | 100 |
| 15th day | 151.6 | 101.1 | 149.4 | 99.6 | 145.3 | 100.9 |
| 1 month | 150.2 | 100.1 | 148.2 | 98.8 | 142.2 | 98.8 |
| 3 months | — | — | — | — | 134.1 | 93.1 |

TABLE 8

The stability of budesonide at 40° C. (content units µg/mL):

| Day | Glass Vial with Spray pump cap Vertical Storage | Budesonide content (%) | Glass Vial with Spray pump cap Horizontal Storage | Budesonide content (%) | Glass Vial with Cap | Budesonide content (%) |
|---|---|---|---|---|---|---|
| 0 day | 150.0 | 100 | 150.0 | 100 | 144.0 | 100 |
| 15th day | 143.9 | 95.9 | 137.8 | 91.9 | 139.8 | 97.0 |
| 1 month | 139.0 | 92.7 | 133.6 | 89.1 | 132.3 | 91.9 |
| 2 months | — | — | — | — | 124.9 | 86.7 |
| 3 months | — | — | — | — | 115.5 | 80.2 |

The data of concentration of budesonide after months of storage at different temperatures (5° C., 25° C., 30° C., 40° C.), have suggested that stable combination formulations have been achieved for budesonide combinations with PVP-Iodine. The concentration of budesonide at different temperatures showed no significant degradation after 6 months at room temperature. The data showed good stability of the budesonide.

Accelerated Degradation Test of PVP-I in the Sample and in the Control (without Budesonide) at 60° C. Using Titration

TABLE 9

| Day | Sample average % w/w Available iodine | Available iodine (%) | Control average % w/w Available iodine | Available iodine (%) |
|---|---|---|---|---|
| 0 day | 0.9822 | 100 | 1.0064 | 100 |
| 2 days | 0.9628 | 98.02 | 0.9608 | 95.46 |
| 3 days | 0.9385 | 95.55 | 0.9284 | 92.25 |
| 8 days | 0.9159 | 93.25 | 0.9150 | 90.92 |

The data of the accelerated degradation test of available iodine in the PVP-Iodine combination formulation in the sample and in the control sample (without budesonide) at 60° C., have suggested that the sample showed a better stability than the control sample, indicating stable combination formulations have been achieved for budesonide combinations with PVP-Iodine. Therefore, satisfactory stability of available iodine was obtained.

Accelerated Degradation Test of Budesonide Content (HPLC) in the Sample and in the Control (without PVP-Iodine) at 60° C. Using Titration

TABLE 10

| Day | Sample (μg/mL) | Budesonide content (%) | Control (μg/mL) | Budesonide content (%) |
|---|---|---|---|---|
| 0 day | 140.9 | 100 | 143.8 | 100 |
| 2 days | 131.2 | 93.1 | 133.4 | 92.8 |
| 3 days | 118.5 | 84.1 | 125.8 | 87.5 |
| 8 days | 106.4 | 75.5 | 126.3 | 87.8 |

The data of the accelerated degradation test of budesonide in the sample and in the control (without PVP-Iodine) at 60° C., have suggested that the sample showed a comparable stability with the control sample, but during the test, it is surprising that we observed that the sample was much more homogeneous than the control. This illustrated the solubility of the budesonide was significantly improved by addition of PVP-Iodine.

Example 8

Studies of Efficacy on Established Bacterial Biofilms

Preparation of PVP-1/Budesonide Suspension.

The test formulation consisted of a 10.0% povidone-iodine 10.6 mg budesonide (PVP-I/B) suspension in 4 mL water (ASL Pharmacy, Camarillo, CA). This concentrated 10% PVP-I/B suspension maintained room-temperature stability for at least 3 months and was self-preserved. The 4 mL suspension was diluted prior to testing with an additional 200 mL of water in a procedure identical to the one employed by patients preparing the same dilute suspension for use as sinonasal irrigation. The resulting extremely dilute (0.2%) PVP-I concentration was chosen based on reported antimicrobial efficacy in vitro, the known pharmaceutical chemistry of PVP-I topical solutions and prior safety studies demonstrating no effect on ciliary beat frequency and the absence of cytotoxicity. The concentration of budesonide was chosen to be consistent with published irrigation trials demonstrating safety and efficacy at a similar cumulative daily dose.

Challenge Organism Preparation:

Planktonic bacterial samples of Staphylococcus aureus (ATCC #6538) and Psuedomonas aeruginosa (ATCC #9027) were obtained from ATCC (Manassas, VA). A sterile swab of S. aureus or P. aeruginosa was aseptically taken from stock cultures maintained at 2-8° C. and aseptically transferred to sterile Trypytic Soy Agar (TSA) slants. The fresh slants were incubated at 30-35° C. for 18-24 hours. Sterile TS saline 10 mL was pipetted into each slant subsequent to incubation and the growth was mechanically dislodged with a sterile cotton-tipped applicator. The suspension was transferred to a sterile 50 mL polypropylene centrifuge tube, washed by centrifugation at 4000×g for 8-10 minutes, supernatant decanted and pellet resuspended in 10 mL saline TS. The resulting suspension was washed a second time, resuspended in 10 mL saline TS and adjusted to an organism concentration of ≈108 cfu/mL.

Optimization:

Three 50 mL conical tubes were filled with approximately 30 mL TSB inoculated at a level of ≈105 cfu/mL of each challenge organism Innoculation controls were prepared containing no coupons for growth comparison. Innoculated tubes were placed on an orbital shaker set to 120 rpm and incubated at 30-37±2° C. for 24±4 hours. Following incubation, biofilms were recovered and enumerated as below.

Sample Preparation and Challenge:

Three samples per challenge organism and three controls each were prepared, inoculated and incubated as in the optimization step above. Following incubation the coupons were aseptically removed from their respective 50 mL conical tubes, gently rinsed with sterile TS saline to remove any loosely adhered planktonic cells and placed into new individual sterile 50 mL conical tubes. For each challenge organism, three samples were placed into 10 mL of sterile saline and 3 were challenged with 10 mL of the test PVP-I/B suspension. After 10 minutes of contact time, 10 mL of Dey-Engly Neutralizing Broth (DEB) was added to all tubes to prevent further antimicrobial action.

Neutralization:

For each test suspension, the test product was diluted 1:10 using DEB. A control sample of 10 mL sterile TS saline was prepared for comparison. Both tubes were inoculated with sufficient inoculums to result in 10-100 cfu of challenge organisms per plate. Inoculated tubes were incubated at 10 minutes to allow for neutralization at ambient temperature. Appropriate aliquots from each tube were plated in duplicate with TSA. The recovery in the neutralizer broth was at least 50% of the recovery in the control samples. Following neutralization, samples were recovered and enumerated as below.

Recovery and Enumeration of Organisms:

Following incubation, test samples and controls were removed from their respective tubes, gently rinsed and the organisms removed from the test surfaces and controls through sonication. Serial dilution of the recovered organisms was performed and the recovered organisms were then quantified.

Results:

The log reductions in viable organisms post-exposure for PVP-I/B and saline controls are presented in Table 11 and Table 12. The average log reduction in viable *P. aeruginosa* from a treated biofilm is 3.9. The average log reduction in viable *S. aureus* from a treated biofilm is 4.2.

TABLE 11

Reduction in Recoverable Organisms From *P. Aeruginosa* Biofilms

| | Saline Exposed Controls | | | | | PVP-I/Budesonide | | | |
|---|---|---|---|---|---|---|---|---|---|
| Dilution | CFU Recovered | | Dilution Corrected AVG | LOG AVG | Dilution | CFU Recovered | | Dilution Corrected AVG | LOG AVG | LOG AVG vs Control |
| $10^{-5}$ | 29 | 25 | $2.7 \times 10^6$ | 6.4 | $10^{-2}$ | 5 | 2 | 350 | 2.5 | 3.9 |
| $10^{-5}$ | 18 | 28 | $2.3 \times 10^6$ | 6.4 | $10^{-2}$ | 14 | 21 | 1750 | 3.2 | 3.2 |
| $10^{-5}$ | 14 | 12 | $1.3 \times 10^6$ | 6.1 | $10^{-2}$ | 9 | 7 | 800 | 2.9 | 3.2 |

TABLE 12

Reduction in Recoverable Organisms From *S. Aureus* Biofilms

| | Saline Exposed Controls | | | | | PVP-I/Budesonide | | | |
|---|---|---|---|---|---|---|---|---|---|
| Dilution | CFU Recovered | | Dilution Corrected AVG | LOG AVG | Dilution | CFU Recovered | | Dilution Corrected AVG | LOG AVG | LOG AVG vs Control |
| $10^{-5}$ | 23 | 27 | $2.5 \times 10^6$ | 6.4 | $10^{-2}$ | 1 | 3 | 200 | 2.3 | 4.1 |
| $10^{-5}$ | 22 | 24 | $2.3 \times 10^6$ | 6.4 | $10^{-2}$ | 2 | 2 | 200 | 2.2 | 4.1 |

Example 9

Studies of Efficacy on Established Fungal Biofilms

In a procedure similar to that described in Example 8 (above), the invention was evaluated for efficacy against fungal biofilms established with *Candida albicans*. The results of the assay for efficacy are summarized in Table 13.

TABLE 13

Reduction in Recoverable Organisms From *C. Albicans* Biofilms

| | Saline Exposed Controls | | | | | PVP-I/Budesonide | | | |
|---|---|---|---|---|---|---|---|---|---|
| Dilution | CFU Recovered | | Dilution Corrected AVG | LOG AVG | Dilution | CFU Recovered | | Dilution Corrected AVG | LOG AVG |
| $10^{-3}$ | 31 | 29 | $3.0 \times 10^4$ | 4.48 | $10^{-2}$ | 0 | 0 | 0 | NA |
| $10^{-3}$ | 60 | 65 | $6.25 \times 10^4$ | 4.79 | $10^{-2}$ | 0 | 0 | 0 | NA |
| $10^{-3}$ | 27 | 21 | $2.4 \times 10^4$ | 4.38 | $10^{-2}$ | 0 | 0 | 0 | NA |

Example 10

Povidone-Iodine Irrigation in Human Subjects

The study treatment consists of sinonasal irrigation with a 0.2% PVP-I/0.6 mg budesonide (PVP-I/B) suspension in purified water, prepared via dilution of a preparation identical to Example 8 above, administered through a commercially available low-pressure, high-volume bottle (Sinus Rinse, NeilMed, Santa Rosa, CA). Treatment was administered BID to each nostril for at least 2 weeks. Pre-treatment bacterial and fungal cultures were obtained and compared to cultures obtained at the conclusion of the study.

Results.

A total of five patients were studied. Patient demographics are detailed in Table 13. None of the patients discontinued use due to intolerance. There were no reported adverse reactions to sinonasal irrigation with PVP-I/B. The mean post-treatment improvement in the subjective symptoms as measured by scaled scores on a validated sinonasal outcomes test was 31. Pre-treatment cultures were positive for 5/5 patients with multi-resistant species including MRSA, *Enterococcus, Acenitobacter, Pseudomonas, Propionobacterium, S. viridans, Klebsiella* and *Serratia*. Post-treatment cultures were positive 2/5 patients only for *S. aureus, Pseudomonas* and *Enterococcus* (Table 16).

TABLE 15

Patient Demographics

| Patient | Age | Gender | Diagnosis | Pre-Op Treatment | tPVP-I/B |
|---------|-----|--------|-----------|------------------|----------|
| 001 | 22 | M | CF | ESS/PO & IV Abx | 4 wks |
| 002 | 49 | F | CRS | rESS/PO Abx/ | 3 wks |
| 003 | 57 | M | CRS | ESS/PO Abx | 3 wks |
| 004 | 54 | F | CRS | ESS/PO Abx | 2 wks |
| 005 | 62 | F | CLL/L | Chemo/XRT | 3 wks |

CRS: chronic rhinosinusitis. CF: cystic fibrosis. CLL: chronic lymphocytic leukemia. L: lymphoma. ESS: endoscopic sinus surgery. rESS: revision endoscopic sinus surgery. tPVP-I/B duration of treatment with PVP-I/B. PO Abx: oral antibiotics. IV Abx: intravenous antibiotics.

TABLE 16

Clinical and Microbiological Data

| Patient | preCx | preSnOT | postCx | postSnOT |
|---------|-------|---------|--------|----------|
| 001 | MRSA Ps | 24 | Ps | 17 |
| 002 | KO, Sa, SM | 61 | Neg | 15 |
| 003 | En, AB | 57 | En | 11 |
| 004 | MRSA, PA, SV | 71 | neg | 34 |
| 005 | Sa | 53 | Sa | 36 |

MRSA: methicillin resistant *staph aureaus*. Ps: *pseudomonas auroginosa*. KO: *Klebsiella oxytoca*. Sa: *Staph aureaus*. SM: *Serratia marcescens*. En: *Enterococus Cloacae*. AB: *acenitobacter Baumanni*. PA: *Propionibacterium Acnes*. SV: *Strep viridans*. Neg: negative.

We developed our treatment program to address the common features of CRS across the whole spectrum of the disease—mechanical congestion of the sinus airspaces, infection by micro-organism (bacterial, fungal, biofilm, etc) and host inflammatory response leading to mucosal edema. We have addressed this therapeutic challenge by combining irrigation, antiseptics and anti-inflammatories. This strategy can address the underlying infectious pathology from both planktonic and biofilm sources can alleviate the concomitant inflammatory response and, mechanically clear the congested sinuses. This tripartite approach to chronic sinus disease addresses all causative pathways and chemically reduces the host immune response that leads to prolonged disease.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims. All publications referenced herein are incorporated by reference in their entireties.

What is claimed is:

1. A pharmaceutical composition for treating a sinus inflammation or infection of a patient in need thereof, consisting of:
    water as a carrier;
    an iodine-containing compound, wherein the iodine-containing compound is povidone-iodine, and the concentration of povidone-iodine in a fully constituted aqueous solution ranges from about 0.01% to about 15% by weight/weight or weight/volume percentage based on the total weight or volume of the pharmaceutical composition;
    a steroid, wherein the steroid is budesonide or a salt or ester thereof, and at least 91% of steroid remains in the pharmaceutical composition after the pharmaceutical composition is stored at a temperature in the range of 5-40° C. for a month; and
    optionally one or more agents selected from the group consisting of microcrystalline cellulose, carboxymethyl cellulose sodium, polysorbate 80, disodium edetate, sodium chloride, hydrochloric acid, and sodium hydroxide.

2. The pharmaceutical composition of claim 1, wherein the concentration of povidone-iodine in a fully constituted aqueous solution ranges from about 0.01% to about 10% by weight/weight or weight/volume percentage based on the total weight or volume of the pharmaceutical composition.

3. The pharmaceutical composition of claim 1, wherein the pharmaceutical composition contains the one or more agents, and the total concentration of the one or more agents ranges from about 0.01% to about 2% by weight based on the total weight of the pharmaceutical composition.

4. The pharmaceutical composition of claim 1, wherein the composition is in an aqueous solution and consisting of about 10% (w/w) povidone-iodine and about 0.015% (w/w) budesonide, wherein the weight percentage is based on the total weight of the pharmaceutical composition.

5. The pharmaceutical composition of claim 1, wherein the composition is an aqueous solution and consisting of about 15% (w/w) povidone-iodine and about 0.025% (w/w) budesonide, microcrystalline cellulose and carboxymethyl cellulose sodium; sodium chloride; polysorbate 80; disodium edetate; and hydrochloric acid, or sodium hydroxide, wherein the weight percentage is based on the total weight of the pharmaceutical composition.

6. The pharmaceutical composition of claim 1, wherein the composition is an aqueous solution and consisting of about 10% (w/w) povidone-iodine, about 0.015% (w/w) budesonide, 0.016% (w/w) polysorbate 80; and 0.9% (w/w) NaCl, wherein the weight percentage is based on the total weight of the pharmaceutical composition.

7. A method for treating a sinus inflammation or infection of a patient in need thereof, wherein the method comprises a step of administering to a sinal cavity of the patient in need therefore a pharmaceutical composition of claim 1.

* * * * *